United States Patent
Ettlin et al.

(10) Patent No.: US 10,639,464 B2
(45) Date of Patent: May 5, 2020

(54) DISCHARGER

(71) Applicant: Sulzer Mixpac AG

(72) Inventors: Josef Ettlin, Eichberg (CH); Daniel Strasser, Gossau (CH)

(73) Assignee: SULZER MIXPAC AG, Haag (CH)

( * ) Notice: Subject to any disclaimer, the term of this patent is extended or adjusted under 35 U.S.C. 154(b) by 305 days.

(21) Appl. No.: 15/117,559

(22) PCT Filed: Feb. 10, 2015

(86) PCT No.: PCT/EP2015/052691
§ 371 (c)(1),
(2) Date: Aug. 9, 2016

(87) PCT Pub. No.: WO2015/121215
PCT Pub. Date: Aug. 20, 2015

(65) Prior Publication Data
US 2016/0346525 A1    Dec. 1, 2016

(30) Foreign Application Priority Data

Feb. 11, 2014 (EP) .................................... 14154722

(51) Int. Cl.
*A61M 35/00* (2006.01)
*A61J 7/00* (2006.01)
(Continued)

(52) U.S. Cl.
CPC ............. *A61M 35/003* (2013.01); *A61C 5/62* (2017.02); *A61D 7/00* (2013.01); *A61J 1/2027* (2015.05);
(Continued)

(58) Field of Classification Search
CPC .... A61M 35/003; A61M 35/00; A61M 5/283; A61M 5/288; A61M 5/31571;
(Continued)

(56) References Cited

U.S. PATENT DOCUMENTS 2,453,590 A   11/1948  Poux
3,376,866 A    4/1968  Ogle
(Continued)

FOREIGN PATENT DOCUMENTS

CN       1635919 A    7/2005
CN     102316918 A    1/2012
(Continued)

OTHER PUBLICATIONS

International Search Report dated Apr. 17, 2015 in International Application No. PCT/EP2015/052691, filed Feb. 10, 2015.
(Continued)

*Primary Examiner* — Adam Marcetich
*Assistant Examiner* — Jessica R Arble
(74) *Attorney, Agent, or Firm* — Global IP Counselors, LLP (57) ABSTRACT

A discharger for a fluid includes a housing having proximal and distal ends, a discharge device, the discharge device defining a passage between inlet and outlet openings, a carriage received in an end region of the housing and moveable relative to the housing between starting and discharge positions, in the starting position, the carriage protruding from the proximal end so as to be pushable into the housing and towards the discharge position, and the carriage defining a receiving space to be loaded with a separate container holding a fluid to be discharged, and an activation device configured to establish a flow connection for the fluid from within the receiving space to the inlet opening, the activation device being inoperative when the carriage is in the starting position and with the activation device establishing the flow connection when the carriage is in or being moved toward the discharge position.

27 Claims, 2 Drawing Sheets

(51) Int. Cl.
*A61J 1/20* (2006.01)
*A61C 5/62* (2017.01)
*A61D 7/00* (2006.01)
*A61M 5/28* (2006.01)
*A61M 5/315* (2006.01)

(52) U.S. Cl.
CPC ............ *A61J 7/0053* (2013.01); *A61M 35/00* (2013.01); *A61M 5/283* (2013.01); *A61M 5/288* (2013.01); *A61M 5/31571* (2013.01)

(58) Field of Classification Search
CPC ........ A61M 2005/2403; A61M 5/2455; A61M 2210/1475; A61M 31/00; A61M 5/24; A61M 2005/2073; A61M 5/3271; A61M 2005/2411; A61J 1/2027; A61J 7/0053; A61C 5/62; A61D 7/00
See application file for complete search history.

(56) References Cited

U.S. PATENT DOCUMENTS

| | | | | |
|---|---|---|---|---|
| 4,767,413 | A | 8/1988 | Haber et al. | |
| 5,843,043 | A * | 12/1998 | Markus | A61M 31/00 604/239 |
| 5,997,512 | A * | 12/1999 | Shaw | A61M 5/3232 604/195 |
| 6,361,552 | B1 * | 3/2002 | Badalamenti | A61J 17/02 606/235 |
| 2002/0169421 | A1 * | 11/2002 | McWethy | A61M 5/3257 604/192 |
| 2003/0088217 | A1 * | 5/2003 | Bergeron | A61M 31/00 604/228 |
| 2007/0108235 | A1 * | 5/2007 | Sogaro | A61J 1/067 222/209 |
| 2011/0301548 | A1 | 12/2011 | Young | |
| 2015/0150760 | A1 * | 6/2015 | Oelz | A61M 5/2466 604/191 |
| 2016/0318051 | A1 * | 11/2016 | Petit | A61J 1/2096 |

FOREIGN PATENT DOCUMENTS

| | | | | |
|---|---|---|---|---|
| GB | 2467904 | A | | 8/2010 |
| JP | S508273 | B1 | | 4/1975 |
| JP | S5146316 | Y2 | | 11/1976 |
| JP | S63290577 | A | | 11/1988 |
| JP | 2012517845 | A | | 8/2012 |
| WO | 9944653 | A1 | | 9/1999 |
| WO | WO2001000261 | | * | 1/2001 ............ A61M 5/315 |
| WO | 02074361 | A2 | | 9/2002 |

OTHER PUBLICATIONS

International Preliminary Report on Patentability and Written Opinion dated Aug. 16, 2016 in International Application No. PCT/EP2015/052691, filed Feb. 10, 2015.

European Office Action dated Feb. 15, 2019 in corresponding EP Patent Application No. 15703584.1.

Japanese Office Action dated Nov. 21, 2018 in corresponding JP Application No. 2016-551202 (with English Translation).

Chinese Office Action dated Dec. 13, 2018 in corresponding Chinese Patent Application No. 201580008003.2 (with English Translation).

Japanese Office Action dated Sep. 3, 2019 in corresponding JP Patent Application No. 2016-551202 (with English Translation).

* cited by examiner

DISCHARGER

CROSS-REFERENCE APPLICATION

This application is a U.S. National Stage Application of International Application No. PCT/EP2015/052691, filed Feb. 10, 2015, which claims priority to European Application No. 14154722.4, filed Feb. 11, 2014, the contents of each of which is hereby incorporated herein by reference.

BACKGROUND

Field of Invention

The present disclosure relates to a discharger for discharging a predetermined amount of fluid, in particular a liquid including at least one medical, dental or veterinary agent. The present disclosure also relates to a container for a discharger as disclosed herein, the container including a predetermined amount of fluid to be discharged by the discharger. Further, the present disclosure relates to a discharge system comprising a discharger and at least one container as disclosed herein.

Background Information

Generally, dischargers such as expendable syringes for use in the medical, dental or veterinary field are known which comprise one or more compartments in which the medical, dental or veterinary agent or a liquid including the medical, dental or veterinary agent is contained before use. The compartment is sealed through components of the discharger which are sealingly fitted into each other or which are provided with specific sealing means such as o-ring gaskets or integrally formed circumferential sealing lips or sealing beads. This way of sealing, however, results in a relatively poor protection of the agent from environmental influences which in turn leads to a limited storage life of the agent and thus to a reduced practical storage life of the discharger itself.

SUMMARY

Before this background, one object of the present disclosure is to provide a discharger for discharging a predetermined amount of fluid which enables an easy and reliable usage and which at the same time improves the protection of the fluid from environmental influences so as to extend the storage life of the fluid and the discharger as compared to prior art devices.

The present disclosure provides such a discharger, a container for the discharger as well as a discharge system as defined in the independent claims.

Accordingly, one aspect of the present disclosure relates to a discharger comprising a housing defining a longitudinal axis and having a proximal end and a distal end, comprising a discharge device arranged at least partly inside the housing and having an inlet opening situated inside the housing and an outlet opening, the discharge device further defining a discharge passage for the fluid extending between the inlet opening and the outlet opening, comprising a carriage received in a proximal end region of the housing and being movable relative to the housing along the longitudinal axis between a starting position and a final discharge position, wherein in the starting position the carriage protrudes from the proximal end of the housing so as to be pushable by a user further into the housing and towards the final discharge position, and wherein the carriage defines a receiving space which is adapted to be loaded with a separate container holding an amount of fluid to be discharged, and comprising an activation means or device for establishing a flow connection for the fluid from within the receiving space of the carriage to the inlet opening of the discharge device, the activation device being inoperative when the carriage is in the starting position and being adapted to establish the flow connection when the carriage is in the final discharge position or is being moved towards the final discharge position.

According to another aspect of the present disclosure, a container is provided which includes a predetermined amount of fluid to be discharged by the discharger. According to a further aspect of the present disclosure, a discharge system is provided which comprises a discharger and a container as disclosed herein, the container being loaded into or being adapted to be loaded into the carriage of the discharger.

The discharger may be adapted to be used in the medical, dental or veterinary field or in the health care sector, the fluid included in the container in particular being a liquid which includes at least one medical, dental or veterinary agent. The present disclosure is, however, not limited to the medical, dental or veterinary sector and can be used in other appliances in which it is desirable to discharge a predetermined amount of fluid in an easy and reliable manner with the fluid being well-protected against environmental influences.

The present disclosure is not limited to the discharge of fluids such as liquids. Rather, the discharger as disclosed herein may alternatively be adapted or used to discharge a viscous material The concept of the present disclosure is to avoid a direct storage of the fluid inside the discharger itself. Consequently, a practically unlimited storage life of the discharger is achieved. By providing a carriage with a receiving space, a separate container can be loaded into the discharger. This concept allows for an easy and yet reliable single-hand operation of the discharger since the flow connection from the container being loaded into the receiving space of the carriage to the inlet opening of the discharge device may be automatically established by the activation device of the discharger.

The amount of the fluid included in the container may range between 0.2 and 2 ml. In an embodiment, the amount of the fluid included in the container is 0.5 ml.

In an embodiment the activation device establishes the flow connection when the carriage is on its way between the starting position and the final discharge position so that the fluid can begin to flow through the discharge passage before the carriage reaches its final discharge position. In an alternative embodiment the activation device may require an additional operation step to be performed by the user in order to actually establish the flow connection. In a particularly comfortable and yet reliable embodiment, however, the flow connection is established automatically by moving the carriage towards the final discharge position.

As already mentioned before, in one embodiment the flow connection is established before the carriage reaches the final discharge position. In an alternative embodiment the carriage has to be in its final discharge position for the flow connection to be established, either automatically or through an additional operation step to be performed by the user.

In an embodiment, the activation device is positioned inside the housing so as to protrude into the receiving space when the carriage is being moved from the starting position towards the final discharge position. By protruding into the receiving space, the activation device is able to interact with a container loaded into the receiving space, for example by breaking a seal of the container.

The activation device may include a device for breaking a seal. In particular, these devices are adapted to provide a piercing, penetrating, puncturing and/or perforating action for the seal.

This embodiment has the advantage that a container loaded into the receiving space can be activated automatically in an easy and reliable manner simply by pushing the carriage, including the container, into the housing of the discharger.

Elements, such as wing-like projections, can be formed at an outer side of the housing so that the discharger may be used like a common syringe by holding the discharger with one finger at each projection and with the thumb on a proximal end of the carriage or of a container loaded into the carriage, thereby providing for a comfortable single-hand operation of the discharger.

The discharge device including the inlet opening, the outlet opening and the fluid passage extending between these openings may be, at least partially, formed integrally with the housing of the discharger. In an embodiment, the discharge device may comprise a portion formed integrally with the housing and one or more separate parts which are connected to the integral portion. In such an embodiment, the activation device may be formed by the portion being integral with the housing or by a separate component of the discharge device, or both.

The discharge device may have a proximal end portion generally facing towards the receiving space, the activation device and the inlet opening being formed at or being integrated into the proximal end region. The proximal end region may be, at least partially, formed integrally with the housing.

In order to enable an easy loading of the container into the carriage, the carriage may have a proximal end having an insertion opening, the receiving space being accessible through the insertion opening, wherein the carriage is adapted to be loaded with the container by sliding the container through the insertion opening into the receiving space. The receiving space may be adapted or matched to the container such that a proximal end face of the container, when loaded into the carriage, is flush with the proximal end of the carriage. In this way, the carriage and the loaded container form a common proximal end face to be acted upon by a user like a push button.

In a further embodiment, the discharge device is adapted to guide the carriage along the longitudinal axis when the carriage is being moved from the starting position towards the final discharge position. Guiding the carriage is an additional function which is imparted to the discharge device in this embodiment. The mechanical stability and reliability are improved by guiding the carriage.

The discharge device may have a proximal end portion including the inlet opening and the carriage may have a distal opening, wherein the discharge device may extend with its proximal end portion through the distal opening into the carriage. In this embodiment, by extending into the carriage, the discharge device may be used to guide the axial movement of the carriage and at the same time may interact with a container loaded into the carriage in order to establish the flow connection for the fluid in the container.

In particular, the proximal end portion of the discharge device is sealingly fitted into the carriage so as to prevent fluid leakage through the distal opening of the carriage. Fitting the proximal end portion of the discharge device into the carriage eliminates the need for separate sealing elements, thereby providing a simple and effective concept in order to ensure that the fluid from the container flows at least substantially only into the inlet opening and through the discharge passage of the discharge device.

In an embodiment, the proximal end portion of the discharge device has an outer diameter which is smaller than an inner diameter of the carriage in the area of the sealing space. Hereby, a reception space for a wall portion of the container is created, this reception space being disposed around the proximal end portion of the discharge device when the carriage is being moved towards the final discharge position. In addition, this concept leads to an efficient usage of the space available within the housing so as to minimize the outer dimensions of the housing and thus of the discharger as a whole.

In an embodiment, the carriage generally has a multiple-cylinder shape at least comprising a proximal cylindrical portion and a distal cylindrical portion. While the proximal cylindrical portion may define the receiving space for the container, the distal cylindrical portion may be used to guide the carriage within the housing or at least to assist guidance of the carriage while at the same time receiving a proximal end portion of the discharge device.

The proximal cylindrical portion of the carriage may have an outer diameter which is greater than an outer diameter of the distal cylindrical portion of the carriage.

In a further embodiment, the proximal cylindrical portion of the carriage has an inner diameter which is greater than an inner diameter of the distal cylindrical portion of the carriage.

Different inner diameters of the cylindrical portions of the carriage may be used to provide for an additional function of the carriage. In particular, inside the carriage a transition portion may be disposed between the proximal cylindrical portion and the distal cylindrical portion. The transition portion may define a distal end of the receiving space so as to serve as a stop for the container being loaded in the receiving space.

In an embodiment, the discharger further comprises securing means or devices which are adapted to prevent the carriage from being unintentionally moved from the starting position along the longitudinal axis. These securing devices facilitate the handling of the discharger by avoiding unintentional operation of the carriage.

In particular, the securing device may comprise a pin/slot arrangement having at least one pin formed at the carriage and at least one slot formed in a wall of the housing, the pin being guided by the slot. The slot may comprise a first portion extending in a circumferential direction and merging into an axial slot portion extending along the longitudinal axis of the discharger. Such securing device requires the user to rotate the carriage with respect to the housing before the carriage can be pushed into the housing and towards the final discharge position.

Generally, the volume for the fluid within the container may be dimensioned as desired in accordance with the respective intended use. The outer shape and the outer dimensions of the container may be the same for different volumes and thus for different quantities of fluid included within the container.

Before this background, the present disclosure also relates to a set of a plurality of containers having at least substantially identical outer shapes and outer dimensions but being different from each other regarding the volume or quantity of contained fluid.

The outer shape of the container may be generally cylindrical.

In an embodiment, the fluid inside the container is protected from environmental influences by a breakable seal.

The container may have a distal end face at least part of which being formed by a breakable seal.

The seal may be formed by a portion of an outer wall of the container, the seal portion having a thickness being smaller than that of other portions of the wall. In an alternative embodiment, the outer wall of the container defines an opening which, after filling the fluid into the container, is closed by a separate sealing element. This sealing element may be in the form of a foil or a film.

The discharger of the present disclosure may include a set of different carriages which differ from each other regarding the size and/or the shape of the receiving space. This enables the discharger to be loaded with different containers so as to enhance the discharger's range of use. Alternatively, a set of inserts may be provided, each insert being matched to a specific type of container so as to adapt the carriage to a specific type of container by inserting the insert into the carriage. In other words, a single carriage may be matched to different containers by using specific adapters to be inserted into the carriage.

In a further embodiment, the discharge device of the discharger has a proximal end portion including the inlet opening, the proximal end portion being sealingly fitted into the container when the carriage is moved towards the final discharge position, so as to prevent at least substantially fluid leakage out of the container past the discharge device. Fitting the proximal end portion into the container also assists in guiding the carriage and thus the container when the carriage is pushed into the housing.

The container may have a cylindrical wall portion which has a thickness being at least approximately the same as the difference between the inner diameters of a proximal cylindrical portion and a distal cylindrical portion of the carriage. In this embodiment, when the container is loaded into the carriage, the distal cylindrical portion of the carriage and the container together may define a cylindrical space having a constant inner diameter which may be at least substantially the same as the outer diameter of a proximal end portion of the discharge device. Thus, when the carriage, including the loaded container, is pushed into the housing, the proximal end portion of the discharge device, starting from the distal cylindrical portion of the carriage, gets into the container, thereby permanently guiding the carriage being moved into its final discharge position.

In an embodiment, the discharge device has a proximal end portion including the inlet opening and the container has an inner wall confining a fluid space of the container, wherein the inner wall comprises a proximal end section, and wherein the proximal end portion of the discharge device and the proximal end section of the inner wall being shaped at least approximately complementary to each other. In this embodiment, the fluid space of the container is more or less completely filled by the discharge device so that the residual amount of fluid contained within the fluid space is minimized when the carriage is in its final discharge position.

In another aspect, the present disclosure also relates to the use of a discharger as disclosed herein or of a discharge system as disclosed herein, for discharging a liquid including at least one medical, dental or veterinary agent, wherein in particular the amount of the liquid lies in the range of 0.2 to 2 ml and preferably is approximately 0.5 ml.

Further embodiments of the present disclosure are also indicated in the description, in the claims as well as in the drawings.

The different embodiments of the discharger, the container and the discharge device described above as well as the individual features which are disclosed there and/or which are mentioned in the dependent claims may be combined with each other.

BRIEF DESCRIPTION OF THE DRAWINGS

The invention will be explained in more detail hereinafter with reference to the drawings.

DETAILED DESCRIPTION OF THE EMBODIMENTS

In the embodiment shown in FIGS. 1 to 6, the discharge system comprises a discharger 10 into which a separate container 25 having a generally cylindrical outer shape can be loaded.

Although other appliances are possible, in the embodiment shown the discharger 10 is intended for use in the medical, dental or veterinary field, and indeed for discharging a predetermined amount of fluid 27 (FIG. 4) which is contained inside the container 25. The fluid to be discharged is a liquid which includes one or more medical, dental or veterinary agents.

The discharger and the container are designed as disposable articles intended for onetime use only.

The container 25 is made as a capsule which has a generally cylindrical outer shape. The container 25 comprises a wall portion 41 (FIG. 5) with an integral proximal end portion providing a proximal end face, and with an opening at the distal end, this opening being closed by a breakable seal 31 in the form of a foil. The wall portion 41 and the seal 31 confine a fluid space of the container which is at least partly filled with the fluid 27. The amount of the fluid is for example 0.5 ml.

Figures 1, 2, 3:
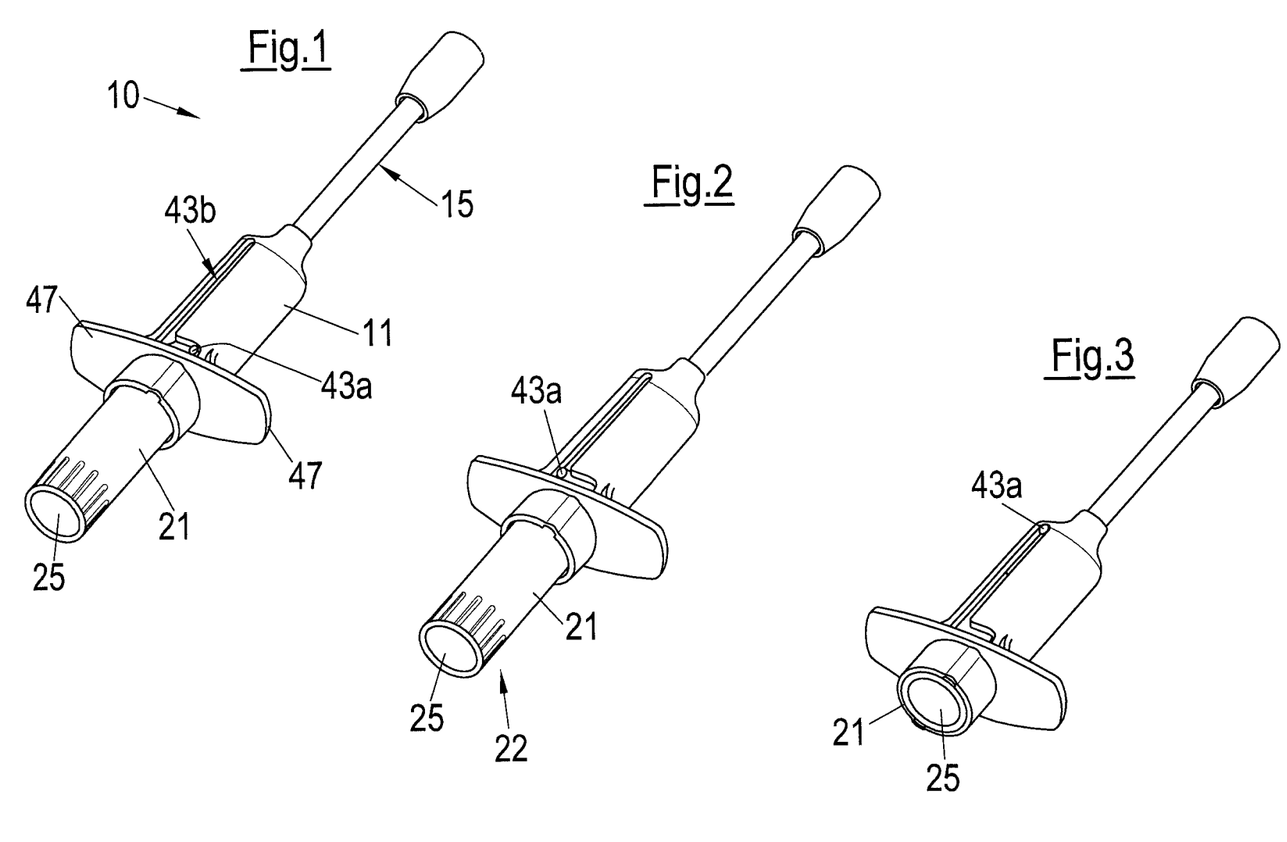
FIGS. 1 to 3 show a discharge system comprising a discharger and a container according to the present disclosure in different states of use.

In a ready-to-use state as shown in FIG. 1, the container 25 has been loaded into a carriage 21 of the discharger 10. To be loaded into the carriage 25, the container 25 is slid through a proximal insertion opening 33 of the carriage 21.

The carriage 21 is received in a proximal end region of a housing 11 which includes wing-like protrusions 27 extending in opposite directions like in a common disposable syringe. Moreover, a slot 43b is formed in the housing 11 which cooperates with a pin 43a formed at the carriage 21 so as to form securing devices which are explained later in more detail.

Figures 4, 5, 6:
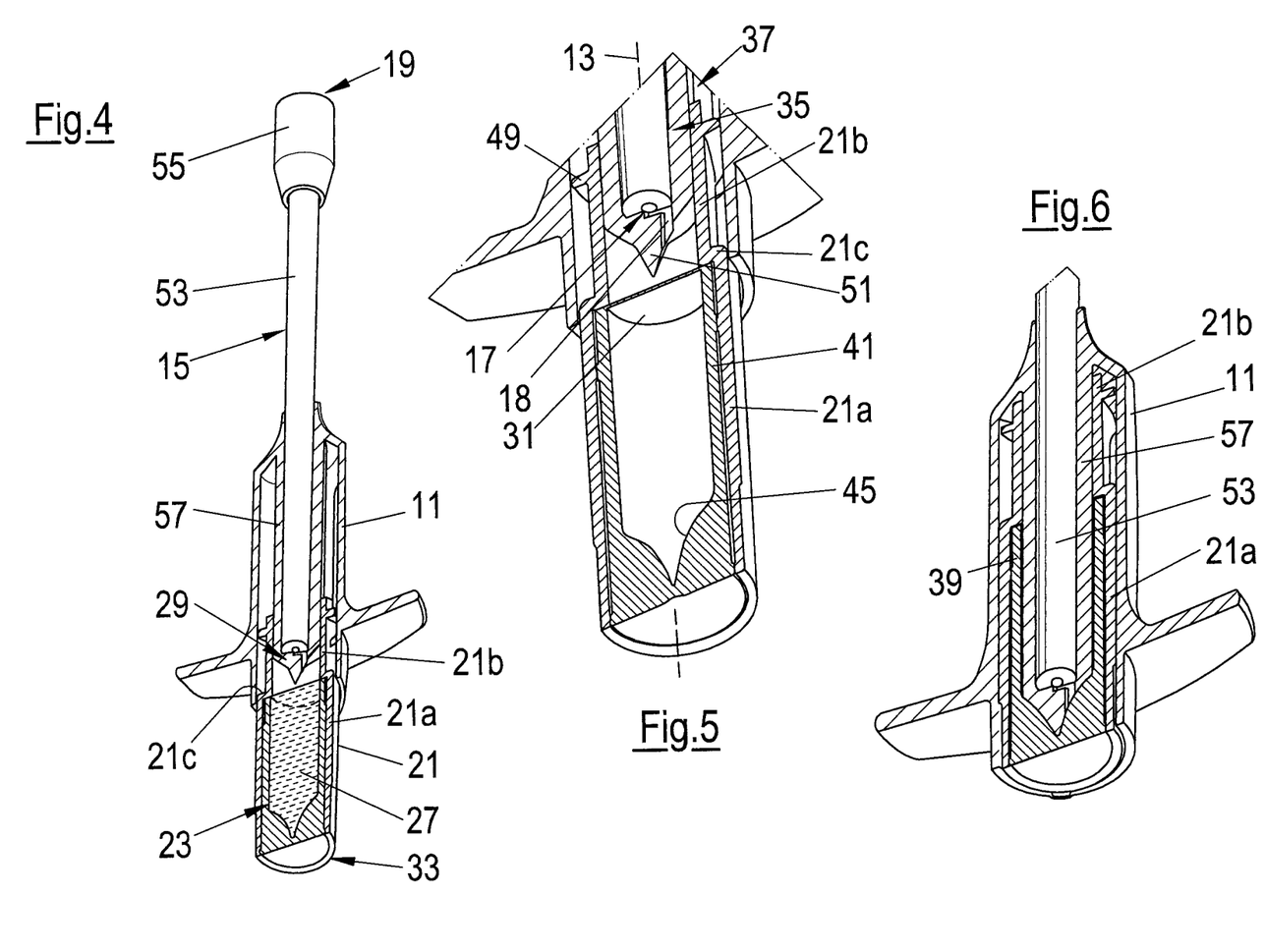
FIG. 4 shows a sectional view along the longitudinal axis of the discharge system of FIG. 1.
FIG. 5 shows an enlarged portion of FIG. 4.
FIG. 6 shows a sectional view along the longitudinal axis of a proximal portion of the discharge system of FIG. 3.

The discharger 10 also comprises a discharge device 15 from which FIGS. 1 to 3 show a tube 53 (FIG. 4) extending from within the housing 11 towards a thickened distal end portion 55 (FIG. 4). The end portion 55 can be integral with the tube 53 or made as a separate component connected in a suitable manner to the tube 53.

The discharger 10 is adapted to discharge the fluid 27 inside the container 25 through the discharge device 15 simply by pushing the carriage 21 including the container 25 into the housing 11. This process is described elsewhere in connection with FIGS. 4 to 6.

The securing devices 43a, 43b prevent the carriage 21 from being pushed into the housing 11 unintentionally. In an initial condition shown in FIG. 1, the pin 43a of the carriage 21 is situated at the end of a circumferential portion of the slot 43b (FIG. 2). This condition prohibits a movement of the carriage 21 along the longitudinal axis 13 (FIG. 5) of the discharger 10.

In order to discharge the fluid, the user must deliberately rotate the carriage 21 with respect to the housing 11 so as to align the pin 43a with an axial portion of the slot 43b (FIG. 2). In order to facilitate the rotation of the carriage 21, the outer wall of the carriage 21 includes longitudinal grooves 22.

In FIG. 2, the carriage 21 is in a starting position and ready to be pushed into the housing 11.

FIG. 3 shows a condition in which the carriage 21 is in a final discharge position in which the carriage 21 and thus the loaded container 25 are fully received within the housing 11, the proximal end faces of the carriage 21 and the container 25 being flush with a proximal end face of the housing 11.

From FIGS. 1 to 3 it can be seen that the carriage 21 and the container 25 together can be actuated like a push button which is to be pressed by a user with her or his thumb while counteracting this pressing actuation by holding the housing with two fingers behind the projections 47.

As shown in FIG. 4, the discharge device 15 comprises a sleeve portion 57 formed integrally with the housing 11 and being arranged inside the housing 11. Further, the discharge device 15 comprises the tube 53 mentioned above which is fitted into the sleeve portion 57.

A proximal end portion 35 (FIG. 5) of the discharge device 15 is fitted into a distal cylindrical portion 21b of the carriage 21 through a distal opening 37 thereof. The proximal end portion 35 comprises an inlet opening 17 at the proximal end of the tube 53, an inlet passage 18 formed at the proximal end of the sleeve portion 57 and activation device 29 (FIG. 4) comprising a tip 51 (FIG. 5) formed by a correspondingly tapering of the proximal end of the sleeve portion 57. In the initial condition shown in FIG. 4, the tip 51 is still positioned spaced apart from the seal 31 of the container 25, i.e. the activation device 29 comprising the tip 51 do not yet protrude into a proximal cylindrical portion 21a of the carriage 21 which defines a receiving space 23 of the carriage 21 for the container 25.

An axial portion of the inlet passage 18 extends offset from the longitudinal axis 13 and leads to a radial portion of the inlet passage 18 which leads into the inlet opening 17 of the tube 53.

A discharge passage extending through the tube 53 connects the inlet opening 17 with an outlet opening 19 (FIG. 4) disposed at the distal end of the discharge device 15.

As can be seen especially in FIGS. 4 and 6, the housing 11 generally has a cylindrical outer shape with a constant inner diameter which is equal to the outer diameter of the proximal cylindrical portion 21a of the carriage 21. In order to conform also the distal cylindrical portion 21b, the outer diameter of which being smaller than that of the proximal cylindrical portion 21a, to the inner diameter of the housing 11, a flange 49 is formed integrally with the distal cylindrical portion 21b.

Moreover, the thickness of the wall portion 41 of the container 25 corresponds to the difference between the inner diameters of the cylindrical portions 21a, 21b of the carriage 21. Consequently, the container 25 reduces the inner diameter of the proximal cylindrical portion 21a to that of the distal cylindrical portion 21b, thereby establishing an inner space of the carriage 21 having a constant inner diameter which corresponds to the outer diameter of the proximal end portion 35 of the discharge device 15.

This dimensioning of the individual components of the discharge system provides for a mechanically reliable mutual guiding of the individual components when the carriage 21 including the container 25 is pushed into the housing. Specifically, the carriage 21 is guided by the inner wall of the housing 11 through its flange 49 and its proximal cylindrical portion 21a. In addition, the carriage 21 is guided by the discharge device 15.

Moreover, the design of the individual components as explained above minimizes the required outer dimensions of the discharger 10, in particular the outer diameter of the housing 11. As can be seen in FIG. 6, there is no unused space inside the housing 11. When the carriage 21 including the container 25 is in the final discharge position, all components are concentrically packed within the housing 11.

A transition portion 21c between the proximal cylindrical portion 21a and the distal cylindrical portion 21b of the carriage 21 is formed as a circumferential shoulder which acts as an axial stop for the container 25 when being loaded into the carriage 21. The axial distance between the proximal end face of the proximal cylindrical portion 21a and the transition portion 21c corresponds to the axial length of the container 25.

The outer shape of the tapered proximal end of the discharge device 15 corresponds to a proximal end section 45 of the inner wall of the container 25 so that almost no free space remains inside the container 25 when the carriage 21 including the container 25 is in its final discharged position as shown in FIG. 6. The complementary shapes of the discharge device 15 and the container 25 thus ensure that virtually no residual amounts of fluid remain within the container 25.

Since in many countries pertinent regulations prohibit a simple throwing away of medical, dental or veterinary substances, the lack of substantial residual amounts of fluid as provided by the discharge system as described herein simplifies the disposal of used containers and dischargers in accordance with the respective national regulations.

In operation, in the initial state as shown in FIG. 1 the securing devices 43a, 43b prevent the carriage 21 from being unintentionally pushed into the housing 11.

For discharging the fluid included in the container 25, which has previously been loaded into the carriage 21, the user has to rotate the carriage 21 in order to bring the pin 43a into alignment with the axial portion of the slot 43b (FIG. 2).

The carriage 21 including the container 25 can now be pushed into the housing 11, and indeed from the starting position shown in FIG. 2 into the final discharge position shown in FIG. 3.

When the carriage 21 is being moved along the longitudinal axis 13 into the housing 11, the seal 31 of the container 25 is broken by the tip 51 of the activation device 29 disposed at the proximal end of the discharge device 15. While the carriage 21 continues its movement into the housing 11, the proximal end portion 35 of the discharge device 15 enters into the fluid space of the container 25, thereby urging the fluid 27 out of the container 25. Since the proximal end portion 35 is sealingly fitted into the distal cylindrical portion 21b of the carriage 21, the fluid can only escape through the inlet passage 18 and thus through the discharge passage of the tube 53 of the discharge device 15.

Consequently, while the carriage 21 is still on its way into the final discharge position, the fluid begins to flow through the inlet passage 18 and the inlet opening 17 and through the discharge passage so as to be ejected from the outlet opening 19.

Since the proximal end portion 35 of the discharge device 15 sealingly fits into the fluid space of the container 25 as well, leakage of fluid past the discharge device 15 is prohibited at any time.

Generally, the discharger and/or the container may be fabricated from any suitable material. In one embodiment, the material is plastic. The material may be selected from the group comprising PP, COC, PE, PA, PBT and PMMA. Alternatively, the material may be glass, metal or an alloy.

From the above description, the skilled person will easily appreciate that the discharge system as described herein ensures a simple and reliable single-hand operation for discharging a predetermined amount of fluid such as a liquid containing at least one medical, dental or veterinary agent. Moreover, this discharge system allows for a long-term storage due to the usage of a separate fluid container so that it is no longer necessary to keep the fluid within the discharger itself. Rather, the fluid can be stored over a long period of time within the container which can be closed by a breakable seal in a manner such that the fluid is very well protected from environmental influences.

With respect to one common classification applied in the medical, dental or veterinary field or the health care sector, the discharger and the discharge system as provided for by the present disclosure belong to the group consisting of systems without protection cap.

The invention claimed is:

1. A discharger for discharging a predetermined amount of fluid, the discharger comprising:
    a housing defining a longitudinal axis and having a proximal end and a distal end;
    a discharge device partly arranged inside the housing and having an inlet opening situated inside the housing and an outlet opening situated outside the housing, the discharge device further defining a discharge passage for the fluid extending between the inlet opening and the outlet opening;
    a carriage received in a proximal end region of the housing and being moveable relative to the housing along the longitudinal axis between a starting position and a final discharge position,
    in the starting position, the carriage protruding from a proximal end of the housing so as to be pushable by a user further into the housing and towards the final discharge position, and
    the carriage defining a receiving space configured to be loaded with a separate container holding an amount of fluid to be discharged; and
    an activation device configured to establish a flow connection for the fluid from within the receiving space of the carriage to the inlet opening of the discharge device, the activation device being inoperative when the carriage is in the starting position and with the activation device being configured to establish the flow connection when the carriage is in the final discharge position or is being moved towards the final discharge position, the discharger configured to discharge the fluid inside the container through the discharge device by a discharging action, the discharging action comprising pushing the carriage and the container into the housing simultaneously, and at least during the discharging action, a position of the discharge device is fixed with respect to the housing.

2. The discharger according to claim 1, wherein the flow connection is established automatically by moving the carriage towards the final discharge position, or the flow connection is established before the carriage reaches the final discharge position.

3. The discharger according to claim 1, wherein the activation device is positioned inside the housing so as to protrude into the receiving space when the carriage is being moved from the starting position towards the final discharge position.

4. The discharger according to claim 1, wherein the carriage has a proximal end having an insertion opening, with the receiving space being accessible through the insertion opening, and the carriage is configured to be loaded with the container by sliding the container through the insertion opening into the receiving space, or the discharge device is configured to guide the carriage along the longitudinal axis when the carriage is being moved from the starting position towards the final discharge position.

5. The discharger according to claim 1, wherein the discharge device has a proximal end portion generally facing towards the receiving space, with the activation device and the inlet opening being formed at or being integrated into the proximal end region, or the proximal end portion of the discharge device includes the inlet opening, and the carriage has a distal opening, the discharge device extending with the proximal end portion through the distal opening into the carriage.

6. The discharger according to claim 5, wherein the proximal end portion of the discharge device has an outer diameter which is smaller than an inner diameter of the carriage in an area of the receiving space so as to provide a reception space for a wall portion of the container disposed around the proximal end portion of the discharge device when the carriage is being moved towards the final discharge position.

7. The discharger according to claim 1, wherein the carriage generally has a multiple-cylinder shape at least comprising a proximal cylindrical portion and a distal cylindrical portion, with the proximal cylindrical portion defining the receiving space for the container.

8. The discharger according to claim 7, wherein the proximal cylindrical portion of the carriage has an inner diameter which is greater than an inner diameter of the distal cylindrical portion of the carriage, or a transition portion is disposed inside the carriage between the proximal cylindrical portion and the distal cylindrical portion, with the transition portion defining a distal end of the receiving space and serving as a stop for the container being loaded into the receiving space.

9. The discharger according to claim 1, further comprising a securing device configured to prevent the carriage from being unintentionally moved from the starting position along the longitudinal axis.

10. A container configured for the discharger according to claim 1, the container being the separate container and including
    a predetermined amount of fluid to be discharged by the discharger.

11. The container according to claim 10, wherein the fluid inside the container is protected from environmental influences by a breakable seal, or the container has a distal end face at least a part of which being formed by the breakable seal.

12. A discharge system comprising: the discharger according to claim 1, and the separate container is at least one container including a predetermined amount of fluid to be discharged by the discharger,
the container being loaded into or configured to be loaded into the carriage of the discharger.

13. The discharge system according to claim 12, wherein the discharge device of the discharger has a proximal end portion including the inlet opening, the proximal end portion being sealingly fitted into the container when the carriage of the discharger is being moved towards the final discharge position, so as to prevent at least substantially fluid leakage out of the container past the discharge device, or
the container has a wall portion having a thickness which is at least approximately the same as the difference between inner diameters of a proximal cylindrical portion and a distal cylindrical portion of the carriage of the discharger.

14. The discharge system according to claim 12, wherein the discharge device of the discharger has a proximal end portion including the inlet opening and the container has an inner wall confining a fluid space of the container, the inner wall comprising a proximal end section, and the proximal end portion of the discharge device and the proximal end section of the inner wall are shaped at least approximately complementary to each other so as to minimize a residual amount of fluid contained within the fluid space of the container when the carriage of the discharger is in the final discharge position.

15. A method comprising:
operating the discharger according to claim 1,
to discharge a liquid including at least one medical, dental or veterinary agent.

16. The discharger according to claim 1, wherein
the activation device includes a device configured to break a seal.

17. The discharger according to claim 16, wherein
the device configured to break the seal is configured to pierce, penetrate, puncture or perforate the seal.

18. The discharger according to claim 5, wherein
the proximal end portion of the discharge device is sealingly fitted into the carriage so as to at least substantially prevent fluid leakage through the distal opening of the carriage.

19. The discharger according to claim 7, wherein
the proximal cylindrical portion of the carriage has an outer diameter which is greater than an outer diameter of the distal cylindrical portion of the carriage.

20. The discharger according to claim 9, wherein
the securing device comprises a pin/slot-arrangement having at least one pin formed at the carriage and at least one slot formed in a wall of the housing, with the pin being guided by the slot.

21. The discharger according to claim 20, wherein
the slot comprises a portion extending parallel to the longitudinal axis and a portion extending in a plane running not parallel to the longitudinal axis.

22. A method according to claim 15, wherein
an amount of the liquid is in the range of 0.2 to 2 ml.

23. A method comprising:
operating a discharge system according to claim 12, to discharge a liquid including at least one medical, dental or veterinary agent.

24. A discharger for discharging a predetermined amount of fluid the discharger comprising:
a housing defining a longitudinal axis and having a proximal end and a distal end;
a discharge device partly arranged inside the housing and having an inlet opening situated inside the housing and an outlet opening situated outside the housing, the discharge device further defining a discharge passage for the fluid extending between the inlet opening and the outlet opening;
a carriage received in a proximal end region of the housing and being moveable relative to the housing along the longitudinal axis between a starting position and a final discharge position,
in the starting position, the carriage protruding from a proximal end of the housing so as to be pushable by a user further into the housing and towards the final discharge position, and
the carriage defining a receiving space configured to be loaded with a separate container holding an amount of fluid to be discharged; and
an activation device configured to establish a flow connection for the fluid from within the receiving space of the carriage to the inlet opening of the discharge device, the activation device being inoperative when the carriage is in the starting position and with the activation device being configured to establish the flow connection when the carriage is being moved towards the final discharge position, and after establishment of the flow connection the carriage is pushable further into the housing, such that a proximal end portion of the discharge device enters into the fluid space of the container, the proximal end portion urging the fluid out of the container.

25. The discharge according to claim 24,
wherein the proximal end portion has an outer shape with a cross-section corresponding to a cross-section of an interior area of the container, a position of the proximal end portion relative to the container defining a remaining amount of fluid holdable by the container during discharging.

26. The discharge according to claim 24,
wherein a least during discharging a position of the proximal end portion is fixed with respect to the housing.

27. A method of operating a discharger for discharging a predetermined amount of fluid, the discharger comprising
a housing defining a longitudinal axis and having a proximal end and a distal end;
a discharge device partly arranged inside the housing and having an inlet opening disposed inside the housing and an outlet opening disposed outside the housing, the discharge device further defining a discharge passage for the fluid extending between the inlet opening and the outlet opening,
a carriage received in a proximal end region of the housing and being moveable relative to the housing along the longitudinal axis between a starting position and a final discharge position,
in the starting position, the carriage protruding from the proximal end of the housing so as to be pushable by a user further into the housing and towards the final discharge position and
the carriage defining a receiving space configured to be loaded with a separate container holding an amount of the fluid to be discharged; and an activation device configured to establish a flow connection for the fluid from within the receiving space of the carriage to the inlet opening of the discharge device, the activation device being inoperative when the carriage is in the starting position and the activation device being configured to establish the flow connection when the carriage is in the final discharge position or is being moved towards the final discharge position, the discharger configured to discharge the fluid inside the container through the discharge device by pushing the carriage including the container into the housing, the method comprising:

discharging the fluid by pushing the carriage including the container into the housing.

* * * * *